United States Patent
Rubinstein et al.

(10) Patent No.: US 7,153,987 B2
(45) Date of Patent: Dec. 26, 2006

(54) PROCESS FOR MAKING SILVER BASED EPOXIDATION CATALYSTS AND PROCESS FOR PREPARING AN OLEFIN OXIDE

(75) Inventors: Leonid Isaakovich Rubinstein, Houston, TX (US); Candido Gutierrez, Houston, TX (US)

(73) Assignee: Shell Oil Company, Houston, TX (US)

( * ) Notice: Subject to any disclaimer, the term of this patent is extended or adjusted under 35 U.S.C. 154(b) by 306 days.

(21) Appl. No.: 10/677,647

(22) Filed: Sep. 30, 2003

(65) Prior Publication Data

US 2004/0110972 A1 Jun. 10, 2004

Related U.S. Application Data

(60) Provisional application No. 60/414,743, filed on Sep. 3, 2002.

(51) Int. Cl.
*B01J 27/232* (2006.01)
*B01J 23/50* (2006.01)
*C07D 301/10* (2006.01)

(52) U.S. Cl. .................... 549/537; 502/174; 502/347

(58) Field of Classification Search ............... 549/537; 502/174, 347

See application file for complete search history.

(56) References Cited

U.S. PATENT DOCUMENTS

| | | | | |
|---|---|---|---|---|
| 2,615,900 A | 10/1952 | Sears, Jr. | ................ | 260/348.5 |
| 3,962,136 A | 6/1976 | Nielsen et al. | ............... | 252/454 |
| 4,007,135 A | 2/1977 | Hayden et al. | ............. | 525/467 |
| 4,010,115 A | 3/1977 | Nielsen et al. | ............... | 252/454 |
| 4,012,425 A | 3/1977 | Nielsen et al. | ........... | 260/348.5 |
| 4,168,247 A | 9/1979 | Hayden et al. | ............. | 252/476 |
| 4,761,394 A | 8/1988 | Lauritzen | .................... | 502/348 |
| 4,785,123 A | 11/1988 | Pennington | ................ | 549/532 |
| 4,820,675 A | 4/1989 | Lauritzen | .................... | 502/216 |
| 4,833,261 A | 5/1989 | Lauritzen | .................... | 549/536 |
| 4,883,889 A | 11/1989 | Pennington | ................ | 549/532 |
| 4,916,243 A | 4/1990 | Bhasin et al. | ................ | 549/534 |
| 5,057,481 A | 10/1991 | Bhasin | ....................... | 502/208 |
| 5,142,070 A | 8/1992 | Fullington et al. | .......... | 549/532 |
| 5,387,751 A | 2/1995 | Hayden et al. | ............. | 549/534 |
| 5,504,053 A | 4/1996 | Chou et al. | ................ | 502/348 |
| 5,525,741 A | 6/1996 | Sugita et al. | ............... | 549/536 |
| 5,573,989 A | 11/1996 | Sugita et al. | ................ | 502/64 |
| 5,625,084 A | 4/1997 | Pitchai et al. | ............... | 549/536 |
| 5,670,674 A | 9/1997 | Grey | .......................... | 549/533 |
| 5,686,380 A | 11/1997 | Pitchai et al. | ............... | 502/347 |
| 5,698,719 A | 12/1997 | Gaffney et al. | ............. | 549/534 |
| 5,703,254 A | 12/1997 | Gaffney et al. | ............. | 549/536 |
| 5,770,746 A | 6/1998 | Cooker et al. | ............. | 549/534 |
| 5,861,519 A | 1/1999 | Kahn et al. | ................. | 549/536 |
| 5,864,047 A | 1/1999 | Gaffney | ...................... | 549/536 |
| 5,965,480 A | 10/1999 | Cooker et al. | ............. | 502/226 |
| 6,623,649 B1 | 9/2003 | Bister et al. | ................ | 210/763 |

FOREIGN PATENT DOCUMENTS

| | | |
|---|---|---|
| DE | 2640540 C3 | 10/1978 |
| EP | 0003642 B1 | 7/1984 |
| EP | 357292 A1 | 3/1990 |
| EP | 179584 B1 | 3/1992 |
| EP | 1162178 A2 | 12/2001 |
| WO | 00/15333 | 3/2000 |

OTHER PUBLICATIONS

Bosch. E., Kocki, J.K., J. Amer. Chem. Society. 1996. 118. 1319.
International Search Report for TH1908 (PCT) dated Jan. 15, 2004.
International Preliminary Examination Report for TH1908 (PCT).
Mil'man. F.A., Timofeeva et al. Improving Silver Catalysts with Alkali Metal Additives for Propylene Epoxidation Reactions, Izv. Nauch–Issled, Inst. Nefte–Uglekhim, Sin. Irkutsk. Univ. (1969). 11(Pt. 1). p. 33–4 (Russian). (English language translation included).
Ussow. A.. Z. Anorg. Chem. 38, 423. 1904. (English language translation included).
Reiss. T. Luft. G. Chem. Eng. Technol. 21. 1998. (6). p. 491–494.

*Primary Examiner*—Bernard Dentz

(57) ABSTRACT

The invention relates to a process for preparing a catalyst which involves (a) preparing a paste having a uniform mixture of at least one alkaline earth metal carbonate; a liquid medium; a silver bonding additive; and, at least one extrusion aid and/or optionally a burnout additive; (b) forming one or more shaped particles from the paste; (c) drying and calcining the particles; and, (e) impregnating the dried and calcined particles with a solution containing a silver compound. The invention also relates to a process for preparing an olefin oxide comprising reacting a gas composition containing an olefin having at least two carbon atoms with oxygen in the presence of the catalyst composition obtained by the process of this invention.

16 Claims, 4 Drawing Sheets

PROCESS FOR MAKING SILVER BASED EPOXIDATION CATALYSTS AND PROCESS FOR PREPARING AN OLEFIN OXIDE

This application claims priority from Provisional Application 60/414,743 filed Sep. 3, 2002.

FIELD OF THE INVENTION

The invention relates to a process for preparing catalysts useful for the manufacture of alkylene oxides comprising silver deposited on an alkaline earth metal carbonate material support. The present invention also relates to a process for preparing an olefin oxide which process comprises reacting an olefin with oxygen in the presence of a catalyst composition comprising silver deposited on an alkaline earth metal carbonate support.

BACKGROUND OF THE INVENTION

The activity, efficiency, stability, and durability of a catalyst in a reaction, for example, the manufacture of alkylene oxides, depend upon the chemical, physical, and structural properties of the catalyst precursors, i.e., the support material and the support particles, and the nature and distribution of the catalytic material on the support. Desirably, the properties of the support material that enhance catalytic activity are retained by the support particles. In general, the support and catalyst comprising small amounts of the catalytic material on the support have essentially the same physical and structural properties with slight differences.

A need exists for a catalyst support having not only the porosity characteristics necessary for proper catalyst loading but good structural properties as well such as crush strength and attrition resistance. In addition, the material comprising the support preferably should be extrudable, in the green state, into complex shapes when desired to provide, for example, higher surface contact area or lower pressure drop across the reactor bed.

A catalyst support needs to possess, in combination, at least a minimum surface area on which the silver component may be deposited, sufficient water absorption and reasonable crush strength. However, a difficulty in optimizing these characteristics lies in the fact that an improvement in one property can result in a reduction in another. Thus optimization of crush strength, for example, may lead to low porosity.

Typically, support materials made from alkaline earth metal carbonate have relatively poor mechanical properties, particularly poor crush strength. Therefore, there is a need for an alkaline earth metal carbonate support with the porosity characteristics necessary for proper catalyst loading, while having improved mechanical properties, especially crush strength.

SUMMARY OF THE INVENTION

The present invention provides a process for preparing a catalyst which comprises:
(a) preparing a paste comprising a uniform mixture of
   (i) at least one alkaline earth metal carbonate;
   (ii) a liquid medium;
   (iii) a silver bonding additive; and,
   (iv) at least one extrusion aid;
(b) forming one or more shaped particles from said paste;
(c) drying and calcining said particles; and,
(d) impregnating the dried and calcined particles with a solution comprising a silver compound.

The invention further provides a process for preparing an olefin oxide which process comprises reacting an olefin with oxygen in the presence of a catalyst composition prepared in accordance with this invention.

DETAILED DESCRIPTION OF THE INVENTION

Figure 1:
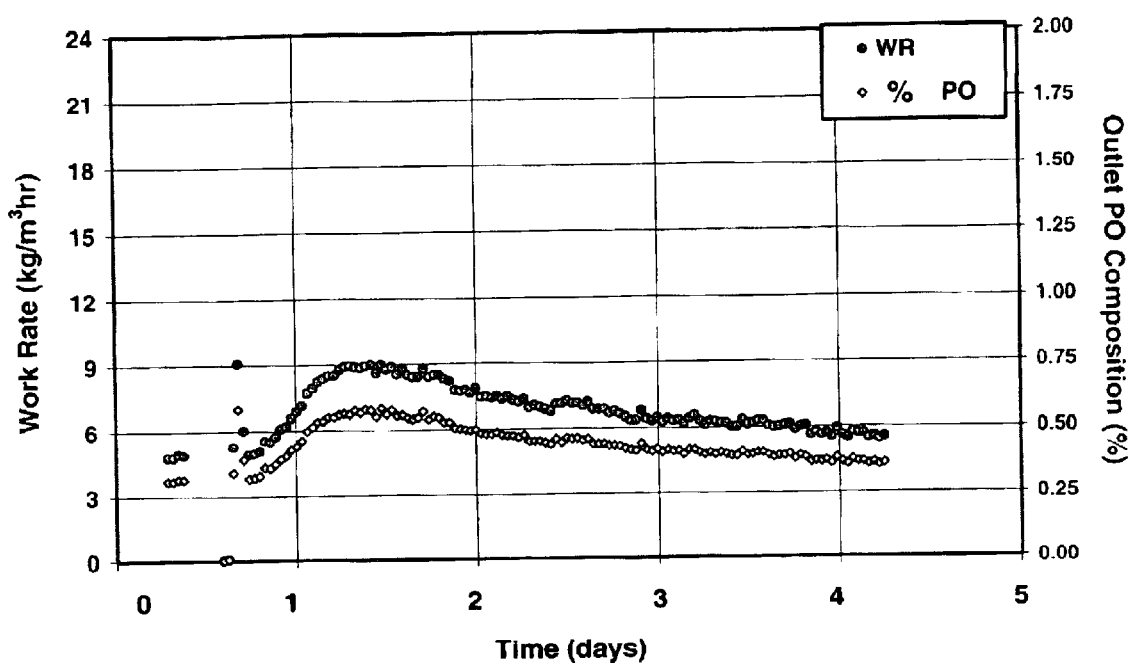
FIG. 1 shows catalyst activity, expressed as work rate (WR), and outlet propylene oxide composition (PO) in the production of propylene oxide using supports without the silver bonding additive.

It has been discovered that the addition of silver, particularly via a silver oxalate ethylenediamine solution, to catalyst support greenware in the course of the preparation of the support, significantly improves the mechanical properties of the support and makes it suitable for commercial use in catalysts useful in olefin epoxidation processes. The term "carrier" may be used interchangeably with the term "support".

The present invention provides a process for making an alkaline earth metal carbonate, preferably a calcium carbonate, catalyst support, having incorporated herein an effective amount of silver to increase the rush strength of the support.

A composition for preparing such catalyst supports having increased crush strength suitably comprises: (a) 80–99% by weight alkaline earth metal carbonate; and, (b) 1–20% by weight silver, calculated as the silver metal. A preferred alkaline earth metal carbonate catalyst support is characterized by a high relative surface area, and a minimum compressive strength of 22N (5 lbs), and preferably comprises 85–89% by weight alkaline earth metal carbonate and 11–15% by weight silver, and more preferably 90–95% by weight of alkaline earth metal carbonate and 5–10% by weight silver.

The alkaline earth metal carbonates supports having high crush strength may be produced by a process which comprises: (a) forming a mixture comprising an alkaline earth metal carbonate, a silver bonding additive, a liquid medium and an organic extrusion aid and optionally a burnout additive to form a paste; (b) forming the paste to produce shaped particles; and (c) drying and calcining the resulting particles. The term "fired" may be used interchangeably with the term "calcined". And, the term "formed" in reference to the support or support particles, may be used interchangeably with the term "shaped".

The alkaline earth metal carbonates may be carbonates such as, for example, magnesium carbonate, or preferably, calcium carbonate. Typically, they have a specific surface area of from 0.5 m²/g to 20 m²/g, preferably 1 m²/g to 18 m²/g, and more in particular from 3 m²/g to 15 m²/g, as measured by the B.E.T. method. Typically, they have an apparent water absorption of from 0.05 ml/g to 2 ml/g, preferably 0.07 ml/g to 1.7 ml/g and more in particular from 0.1 ml/g to 1.5 ml/g, as measured by a conventional water absorption technique. The alkaline earth metal carbonate supports are of particular interest as they provide catalysts which have an improved activity performance over time. The alkaline earth metal carbonate carbonate is suitably a commercially available material and sold by companies such as J. M. Huber and Alfa Inorganic and milled to different average particle sizes typically in the range of 0.5 to 15 microns (median pore diameter).

The liquid medium is typically aqueous, but it may also comprise other liquids, such as alcohols.

The silver bonding additive may preferably be an aqueous silver oxalate amine solution having a concentration of silver from 15% to 33% by weight, preferably from 20% to 33% by weight, and most preferably from 27% to 33% by weight. The preferred amine is ethylenediamine although other diamines such as 1,3-propylene diamine, 1,4-cyclohexane diamine, and 1,4-butylene diamine can be used. The final silver content in the support is in the range of from 1 to 20 parts by weight, preferably from 1 to 15 parts by weight and most preferably from 1 to 10 parts by weight based on 100 parts total weight of the resulting support. The final weight ratio of silver/calcium carbonate typically is from 1:5 to 1:100, specifically from 1:7 to 1:30, more specifically from 1:8 to 1:10, and for example 1:9, with the silver calculated as silver metal.

The supports are preferably prepared by blending from 90 to 100 parts by weight (pbw) alkaline earth metal carbonate with 1–2 pbw of an organic extrusion aid such as starch or petroleum jelly. Then, a sufficient amount of water may be added to make the composition extrudable (this is usually achieved when there is 35–45 pbw silver solution present) and the resulting composition is mixed until homogeneous.

Once the paste is prepared, for example by mulling and, if desired, aging, it is ready for forming, for example by extrusion or spraying. The paste can be formed into an extrudate using an extruder. The extrudate can be any diameter, for example from 0.5 mm to 5 cm, but, for best catalytic activity and ease of handling and processability, the extrudate is preferably from 1 mm to 5 cm in diameter. Larger or smaller diameter extrudates can be prepared, depending on the desired use of the resultant extrudate. After the extrudate passes through the extruder die, the extrudate can be cut into uniform lengths, if desired. However, uniform lengths are not always necessary, so the extrudate can be allowed to break on its own, into any length. If the extrudate is allowed to break on its own, it will usually have a length of 2 to 7 times the diameter width. Usually, the extrudate is allowed to break of its own accord because of ease of manufacture and economics. The support may be formed into shaped particles, for example, chunks, pieces, and the like. Preferably, for use in a tubular fixed bed reactor, they are formed into a rounded shape, for example in the form of spheres, pellets, cylinders, rings, wagon wheels, or tablets, typically having dimensions in the range of from 1 mm to 5 cm.

A broad variety of drying and calcination procedures may be applied. The drying and calcining steps of the present method are in general carried out at temperatures in the range from 100° C. to 1000° C. The shaped support precursor is freed of uncombined and loosely held water by an initial, moderate heating, for example at a temperature in the range from 100° C. to 215° C. Following this drying procedure, the calcination may be carried out in a dry or humid atmosphere at a temperature in the range from 200° C. to 950° C., referably from 220° C. to 850° C., more preferably from 230° C. to 700° C. The calcination may be carried out for period of from 1 hour to 16 hours, or from 1 hour to 12 ours, or from 1 hour to 10 hours. As one non-limiting illustrative example, the extrudate can be dried overnight at 100° C. and then calcined as follows: 1 hour ramp to 110° C. held for 1 hour, then 4 hour ramp to 240° C. and held for 1 hour and finally a 4 hour ramp to 500° C. and held for 5 hours.

In a preferred embodiment, a shaped silver bonded alkaline earth metal carbonate catalyst support may be prepared by: (a) preparing a paste comprising a uniform mixture of (i) calcium carbonate; (ii) at least one solvent; (iii) a silver oxalate ethylenediamine complex; and (iv) at least one extrusion aid; (b) forming a shaped particle from said paste; and (c) drying and calcining said shaped particle, wherein said paste has a weight ratio of said silver to calcium carbonate of approximately from 1:5 to 1:100, specifically from 1:7 to 1:30, more specifically from 1:8 to 1:10, and for example 1:9.

In another preferred embodiment, the support composition is produced by: (a) mixing between 80 to 99 parts by weight calcium carbonate and between 35 to 55 parts by weight aqueous silver oxalate-ethylenediamine solution having a concentration of 27–33% by weight of said silver complex to form a homogeneous mixture; (b) extruding said homogeneous mixture to form an extrudate; and (c) calcining the extrudate at a temperature in the range of from 200° C. to 950° C., preferably from 220° C. to 850° C., more preferably from 230° C. to 700° C. for a period of from 1 hour to 16 hours.

The alkaline earth metal carbonate supports supports have improved crush strength over those alkaline earth metal carbonate supports made without a silver bonding additive. The flat plate crush strength of the supports is typically at least 22N (5 lbs), specifically at least 40N (9 lbs), and more specifically at least 53N (12 lbs). They are particularly useful for preparing alkylene oxides such as ethylene oxide and propylene oxide via silver catalyzed epoxidation of alkenes. They can be used in the manufacture of silver epoxidation catalysts used in the production of ethylene oxide, propylene oxide, butadiene monoepoxide etc.

The catalysts may be prepared from the supports in accordance with methods which are known per se. Suitable methods for preparing the catalyst are known from U.S. Pat. No. 3,962,136 and WO-00/15333, both of which are herein incorporated by reference.

In a suitable method of catalyst preparation, the support is impregnated with a liquid composition of compounds of silver, potassium, sodium and/or lithium and, if desirable with further compounds of, for example, one or more of rubidium and/or, cesium or other useful additives, and subsequently dried by heating at a temperature in the range of from 150° C. to 500° C., in particular of from 200° C. to 450° C. Drying may be performed for a period of from 1 minute to 24 hours, typically from 2 minutes to 2 hours, more typically from 2 to 30 minutes. The atmosphere for drying may be air, an inert gas, such as nitrogen or argon, or steam. The silver compounds which may be used in the liquid composition may be selected from the silver bonding additives as defined herein before.

Reducing agents will generally be present to effect the reduction of a silver compound to metallic silver. For example, a reducing atmosphere, such as a hydrogen or ethylene containing gas, may be employed, or a reducing agent, for example oxalate, may be present in one or more of the impregnation liquids. If desired, the pore impregnation may be carried out in more than one impregnation and drying step. For example, silver may be impregnated in more than one step, and the promoters may be impregnated in one or more separate steps, prior to silver impregnation, after silver impregnation or intermediate to separate silver impregnation steps. The liquid composition is typically a solution, more typically an aqueous solution.

The compounds employed in the impregnation may independently be selected from, for example, inorganic and organic salts, hydroxides and complex compounds. They are employed in such a quantity that a catalyst is obtained of the desired composition.

The catalysts of the present invention are useful for epoxidation of any olefin, which has at least 2 carbon atoms. Typically, the number of carbon atoms is at most 10, more typically at most 5. It is most preferred that the number of carbon atoms is three.

Apart from having an olefinic linkage (i.e. a moiety >C=C<), the olefin may comprise another olefinic linkage, or any other kind of unsaturation, for example in the form of an aryl group, for example a phenyl group. Thus, the olefin may be a conjugated or non-conjugated diene or a conjugated or non-conjugated vinyl aromatic compound, for example 1,3-butadiene, 1,7-octadiene, styrene or 1,5-cyclooctadiene.

In preferred embodiments, the olefin comprises a single olefinic linkage and, for the remainder, it is a saturated hydrocarbon. It may be linear, branched or cyclic. A single alkyl group may be attached to the olefinic linkage, such as in 1-hexene, or two alkyl groups may be attached to the olefinic linkage, such as in 2-methyl-octene-1 or pentene-2. It is also possible that three or four alkyl groups are attached to the olefinic linkage. Two alkyl groups may be linked together such that they form a ring structure, such as in cyclohexene. In these preferred embodiments, a hydrogen atom is attached to the olefinic linkage at the places which are not occupied by an alkyl group. It is particularly preferred that a single alkyl group is attached to the olefinic linkage.

Olefins having at least 3 carbon atoms are, most preferably, 1-pentene, 1-butene and, in particular, propylene. The skilled person will appreciate that, in accordance with the geometry of its molecules, an olefin may yield a mixture of olefin oxides, for example olefin oxides in more than one isomeric form.

Generally, the process of this invention is carried out as a gas phase process, which is a process wherein gaseous reactants are reacted in the presence of a solid catalyst. Frequently, the reactants and any further components fed to the process are mixed and subsequently contacted with the catalyst. The ratio of the quantities of the reactants and the further components, if any, and the further reaction conditions are not material to this invention and they may be chosen within wide ranges. As, generally, the mixture contacted with the catalyst is gaseous, the concentrations of the quantities of the reactants and the further components, if any, are specified below as a fraction of the mixture in gaseous form.

The concentration of the olefin may suitably be at least 0.1% v, typically at least 0.5% v, and, suitably, at most 60% v, in particular, at most 50% v. Preferably, the concentration of the olefin is in the range of from 1% v to 40% v. If the olefin is propylene, 1-butene or 1-pentene it is preferred that its concentration is in the range of from 1% v to 30% v, in particular from 2% v to 15% v.

The concentration of oxygen may suitably be at least 2% v, typically at least 4% v, and in practice the concentration is frequently at most 20% v, in particular at most 15% v. If the olefin is propylene, 1-butene or 1-pentene it is preferred that the concentration of oxygen is in the range of from 0.6% v to 15% v, in particular from 8% v to 15% v. The source of oxygen may be air, but it is preferred that an oxygen containing gas which may be obtained by separation from air is used.

Organic chloride compounds may be added to the mixture as moderators of the catalyst, improving the selectivity. Examples of such organic chloride compounds are alkyl chlorides and alkenyl chlorides. Methyl chloride, vinyl chloride, 1,2-dichloroethane and, in particular, ethyl chloride are preferred organic chloride compounds. The organic chloride compounds may be used at a concentration of at least 0.1 ppm by volume, typically at least 0.2 ppm by volume, preferably at least 1 ppm by volume and at most 20 ppm by volume in the case of ethylene. In the case of propylene, the organic chloride concentration may be at least 20 ppm by volume, more preferably at least 50 ppm by volume, and the concentration may be at most 2000 ppm by volume, in particular at most 1500 ppm by volume, wherein ppm by volume is calculated as the molar quantity of chlorine atoms in the total quantity of the reactant mixture. Thus, 1 ppm corresponds to 1 molecule of ethyl chloride in 1,000,000 molecules of gas.

The performance of the catalyst of the present invention may be improved by adding to the reaction mixture a nitrate or nitrite forming compound. A nitrate or nitrite forming compound is a compound which is capable, under the conditions at which it is contacted with the catalyst, of introducing nitrate or nitrite ions on to the catalyst. In general, the nitrate or nitrite ions tend to disappear from the catalyst during the process, in which case they need to be replenished. As a consequence, it is preferred to add the nitrate or nitrite forming compound continuously to the mixture, or in a discontinuous mode at least at the points in time that the need thereto arises. For the initial stage of the process, it may be sufficient to add the nitrate or nitrite forming compound or nitrate or nitrite ions to the catalyst at the stage of catalyst preparation. Preferred nitrate or nitrite forming compounds are nitric oxide, nitrogen dioxide and/or dinitrogen tetraoxide. Alternatively, hydrazine, hydroxylamine, ammonia or other nitrogen containing compounds may be used. A mixture of nitrogen oxides is preferably used, which may be designated by the general formula $No_x$, wherein x is a number in the range of from 1 to 2, expressing the molar average atomic ratio of oxygen and nitrogen of the nitrogen oxides in the mixture.

In the case of ethylene epoxidation, the nitrate or nitrite forming compound may suitably be used at a concentration of at least 1 ppm by volume, typically at least 5 ppm by volume, and the concentration may suitably be at most 30 ppm by volume, in particular at most 20 ppm by volume, wherein ppm by volume is calculated as the volume of the monomeric nitrate or nitrite forming compound(s) relative to the total volume of the mixture of the reactants and the further components. For propylene epoxidation, the nitrate or nitrite forming compound may suitably be used at a concentration of at least 10 ppm by volume, typically at least 50 ppm by volume, and the concentration may suitably be at most 500 ppm by volume, in particular at most 300 ppm by volume. If rubidium and/or cesium are present in the catalyst used for propylene epoxidation, the nitrate or nitrite forming compound is preferably used at a concentration of at least 10 ppm by volume, in particular at least 20 ppm by volume, and the concentration is typically at most 200 ppm by volume, more typically at most 150 ppm by volume, preferably at most 80 ppm by weight, in particular at most 50 ppm by volume, on the same basis.

Carbon dioxide may or may not be present in the mixture. Carbon dioxide is preferably not present because carbon dioxide reduces catalyst activity and selectivity and, thus, the yield of olefin oxide. Carbon dioxide may typically be present at a concentration of at most 35% v, in particular at most 20% v.

Furthermore, inert compounds may be present in the mixture, for example nitrogen, argon, and/or methane. It is preferred to have methane present, as methane improves the dissipation of the heat of reaction, without adversely affecting the selectivity and the conversion.

The process may preferably be carried out at a temperature of at least 150° C., in particular at least 200° C. Preferably the temperature is at most 320° C., in particular at most 300° C. The process may preferably be carried out at a pressure of at least 0.5 barg (i.e. bar gauge), in particular at least 1 barg. Preferably the pressure is at most 100 barg, in particular at most 50 barg.

In general, it is preferred to operate at a high oxygen concentration. However, in actual practice, in order to remain outside the flammability limits of the mixture of reactants and any further components present therein, the concentration of oxygen may be lowered as the concentration of the olefin is increased. The actual safe operating conditions also depend on individual plant conditions, such as temperature and pressure, and tube sizes. Therefore, in each individual plant, a so-called flammability equation is used to determine the concentration of oxygen which may be used to approximate the allowable oxygen concentration with any concentration of the olefin.

When operating the process as a gas phase process using a packed bed reactor, the Gas Hourly Space Velocity (GHSV) may preferably be at least 100 Nl/l·h, in particular at least 200 Nl/l·h. The GHSV may preferably be at most 30000 Nl/l·h, in particular at most 15000 Nl/l·h. Gas Hourly Space Velocity is the volumetric flow rate of the feed gas, herein defined at normal conditions (i.e. 0° C. and 1 bar absolute), divided by the volume of the catalyst bed.

The catalysts prepared on the calcium carbonate/silver supports described herein above, exhibited superior performance in both activity, selectivity, and stability compared to catalysts made on pure calcium carbonate support. See FIGS. 1–4.

EXAMPLES

The pore volume and the pore size distribution were measured by a conventional mercury intrusion device in which liquid mercury was forced into the pores of the support. Greater pressure is needed to force the mercury into smaller pores, therefore, the measurement of pressure increments corresponds to volume increments in the pores penetrated and hence to the size of the pores in the incremental volume. The pore volume in the following description was determined by mercury intrusion under pressures increased by degrees to a pressure of $3.0 \times 10^8$ Pa using a Micromeritics Autopore 9200 model (130° contact angle and mercury with a surface tension of 0.473 N/m).

Example 1A

Preparation of Silver-amine-oxalate Stock Solution

A silver-amine-oxalate stock solution was prepared by the following procedure: 415 g of reagent-grade sodium hydroxide were dissolved in 2340 ml de-ionized water and the temperature was adjusted to 50° C. 1699 g high purity "Spectropure" silver nitrate was dissolved in 2100 ml de-ionized water and the temperature was adjusted to 50° C. The sodium hydroxide solution was added slowly to the silver nitrate solution, with stirring, while maintaining a solution temperature of 50° C. This mixture was stirred for 15 minutes, then the temperature was lowered to 40° C. Water was removed from the precipitate created in the mixing step and the conductivity of the water, which contained sodium and nitrate ions, was measured. An amount of fresh deionized water equal to the amount removed was added back to the silver solution. The solution was stirred for 15 minutes at 40° C. The process was repeated until the conductivity of the water removed was less than 90 μmho/cm. 1500 ml of fresh deionized water was then added.

630 g of high-purity oxalic acid dihydrate were added in approximately 100 g increments. The temperature was maintained at 40° C. and the pH was maintained at a level above 7.8. Water was removed from this mixture to leave a highly concentrated silver-containing slurry. The silver oxalate slurry was cooled to 30° C. Then, 699 g of 92% w ethylenediamine (8% de-ionized water) were added to the slurry while maintaining a temperature no greater than 30° C. The resulting solution contained approximately 27–33% w silver.

The above stock solution was used to prepare the silver doped calcium carbonate supports as shown in Tables 1 and 2.

Examples 1B–16

Preparation of Samples

The calcium carbonate supports, as exemplified in the Tables 1 and 2, were prepared as follows: 100 parts by weight (pbw) calcium carbonate ($CaCO_3$) mixed with 2 pbw of an organic extrusion aid such as starch. Sufficient water was added to make the mixture extrudable (45 pbw silver solution) and the resulting composition was mixed until homogeneous and extrudable. The resulting paste was forced through a 3 mm die. The resulting extrudate was dried overnight at 100° C. and then fired as follows: 1 hour ramp to 110° C. held for 1 hour, then 4 hour ramp to 240° C. and held for 1 hour and finally a 4 hour ramp to 500° C. and held for 5 hours. The weight ratio of silver as metal to calcium carbonate was 1:9 in all of the Examples in Tables 1 and 2.

For comparison purposes, a calcium carbonate support without silver was prepared as follows: 500 grams of calcium carbonate and 20 grams of an organic extrusion aid such as starch were mixed dry for 30 seconds in a Cuisinart mixer, 350 grams of deionized water were added (20–26 pbw) and the entire mixture was blended for an additional 3 minutes. The resulting paste was extruded using a piston extruder and dried overnight at 110° C. in a lab oven. The extrudate was ramped to 500° C. over 5 hours and held at temperature for 5 hours.

In the discussion that follows, the invention will be discussed in terms of added "silver" because, after the firing operation, it is assumed for the purposes of this application that the silver in the support will be in the form of silver particles in metal (non-cationic) zero oxidation state.

TABLE 1

| Ex. No. | Material | Surface Area (m²/g) | Median Pore Diameter (Angstroms) | Flat Plate Crush Strength (N (lbs)) | Porosity (%) |
|---|---|---|---|---|---|
| 1B | CaCO₃ | 5.1 | 5900 | 5.3 (1.2) | 63 |
| 2 | CaCO₃ | 5.9 | 1818 | 35 (7.8) | 33 |
| 3 | CaCO₃/Ag | * | * | * | 25.3 |
| 4 | CaCO₃/Ag | 3.35 | * | * | 25 |
| 5 | CaCO₃/Ag | 4.3 | * | 19 (4.3) | 47 |
| 6 | CaCO₃/Ag | 3.5 | 3300 | 72.5 (16.3) | 30 |
| 7 | CaCO₃/Ag | 3.6 | 4401 | * | 42 |
| 8 | CaCO₃/Ag | 3.6 | 3484 | * | 35 |
| 9 | CaCO₃/Ag | 3.7 | 3395 | 59.6 (13.4) | 30 |

*not measured

TABLE 2

| Ex. No. | Material | Surface Area (m²/g) | Median Pore Diameter (Angstroms) | Crush Strength (N (lbs)) | Water Pore Volume (cc/g) |
|---|---|---|---|---|---|
| 10 | CaCO₃ | 1.1 | 7200 | 8.9 (2) | .22 |
| 11 | CaCO₃/Ag | 1 | 9000 | 44.9 (10.1) | .227 |
| 12 | CaCO₃ | 2 | 4000 | 28 (6.2) | .23 |
| 13 | CaCO₃/Ag | 1.8 | 4039 | 61.3 (13.8) | .21 |
| 14 | CaCO₃ | 2.7 | 2600 | 36 (8.2) | .24 |
| 15 | CaCO₃/Ag | 2.4 | 2910 | 69.8 (15.7) | .217 |
| 16 | CaCO₃/Ag | 3.7 | 3400 | 59.6 (13.4) | 0.3 |

Example 17
Catalyst Preparation and Testing for Propylene Oxide (PO)

Catalyst 1 was prepared on the support of Example 16 (See Table 2). A cesium doped silver ethylenediamine oxalate solution was made in which 1.258 g of cesium hydroxide was dissolved in 150 g of the silver solution as prepared in Example 1A. The support was first impregnated under vacuo with this cesium doped silver solution, dried in air at 250° C. for 5 minutes, then impregnated again with the cesium doped silver solution and dried at 250° C. for 5 minutes. The resulting material was then impregnated in vacuo with an aqueous solution containing 42.8 g of potassium nitrate, 14.4 g of sodium nitrate, and 1.8 g of lithium hydroxide dissolved in 225 g of water. Upon this last impregnation, the catalyst was dried in air for 5 min. at 250° C. The resulting catalyst contained 34% silver, 500 mmol/g potassium, 200 mmol/g sodium, 50 mmol/g lithium, and 45 mmol/g celsium. Then, the catalyst was ground and sieved to a mesh size of 20–30. Then, 15 g of the sieved catalyst was loaded in a U-shaped microreactor tube.

Testing was conducted at 230° C., under a pressure of 38 psig, and with a flow of 150 cc/min. The gas composition was as follows: 7% propylene, 12% oxygen, 100 ppm $NO_x$ (whereas $NO_x$ corresponds to a mixture of nitric oxide, nitrogen dioxide, and dinitrogen tetroxide), 150 ppm ethylchloride, balance nitrogen. After 24 hours on stream, the effluent contained 0.5% PO, and the catalyst selectivity towards PO based on propylene was measured at 55%.

Example 18
Catalyst Preparation and Testing for Ethylene Oxide (EO)

Catalyst 2 was prepared on the support of Example 11 (See Table 2) as follows. The support was first impregnated with the silver ethylenediamine oxalate solution by vacuum impregnation, and dried at 250° C. for 5 minutes. Then, the support was vacuum impregnated with the solution of 2.32 g of potassium nitrate in 50 g of water, and consequently dried at 250° C. for 5 minutes. The resulting catalyst contained 19.6% silver, and 100 ▢mmol/g potassium. The catalyst was ground and sieved to a mesh size of 20–30. Then 1.75 g of the sieved catalyst was loaded in a U-shaped microreactor tube.

Testing was conducted at a pressure of 210 psig, and a flow rate of 281 cc/min. The gas composition was as follows: 30% ethylene, 8% oxygen, 0.4% carbon dioxide, 5 ppm $NO_x$ (whereas $NO_x$ corresponds to a mixture of nitric oxide, nitrogen dioxide, and dinitrogen tetroxide), 5 ppm ethylchloride, balance nitrogen. The temperature was maintained such that the outlet concentration of ethylene oxide was 1.5%. After 10 days on stream, the selectivity of the catalyst was measured at 90.5% at 250° C.

Example 19
Catalyst Preparation and Testing for Ethylene Oxide (EO)

Catalyst 3 was prepared on the support of Example 15 (Table 2) as follows. The support was first impregnated with the silver ethylenediamine oxalate solution by vacuum impregnation, and dried at 250° C. for 5 minutes. Then, the support was vacuum impregnated with the solution of 7.28 g of potassium nitrate in 50 g of water, and consequently dried at 250° C. for 5 minutes. The resulting catalyst contained 19.2% silver, and 300 ▢mmol/g potassium. The catalyst was ground and sieved to a mesh size of 20–30. Then, 1.75 g of the sieved catalyst were loaded in a U-shaped microreactor tube.

Testing was conducted at a pressure of 210 psig, and a flow rate of 281 cc/min. The gas composition was as follows: 30% ethylene, 8% oxygen, 5 ppm $NO_x$ (whereas $NO_x$ corresponds to a mixture of nitric oxide, nitrogen dioxide, and dinitrogen tetroxide), 5 ppm ethylchloride, balance nitrogen. The temperature was maintained such that the outlet concentration of ethylene oxide was 1.5%. After 8 days on stream, the selectivity of the catalyst was measured at 90.0% at 233° C.

Example 20

Figure 2:
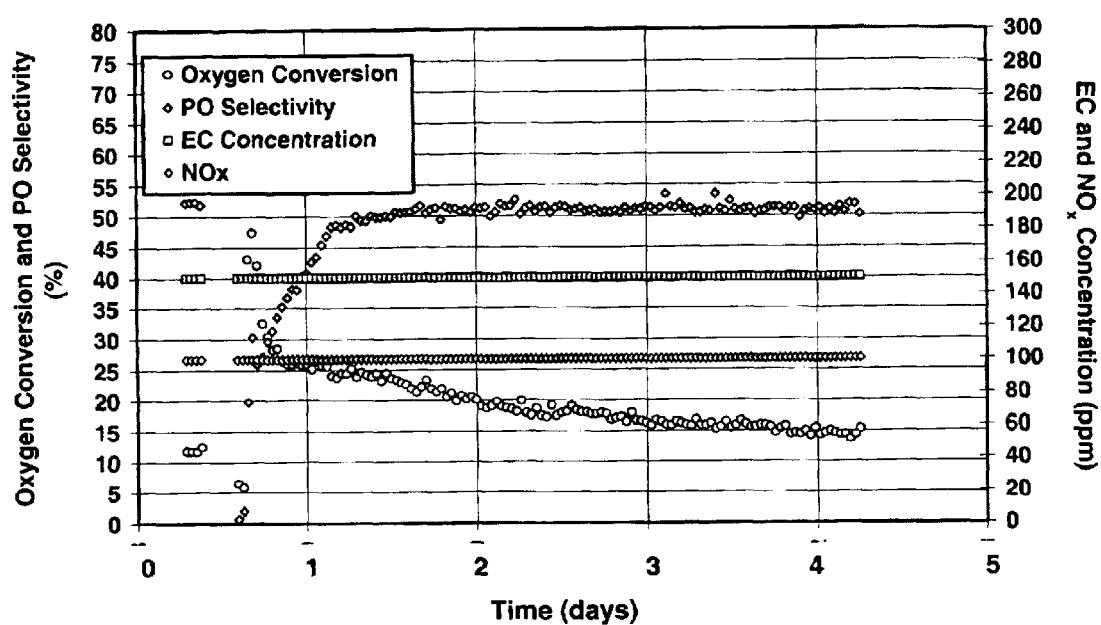
FIG. 2 shows the oxygen conversion, propylene oxide (PO) selectivity, ethylchloride (EC) concentration and $NO_x$ concentration, whereas $NO_x$ is a mixture of nitric oxide, nitrogen dioxide, and dinitrogen tetroxide, using supports without the silver bonding additive.
Figure 3:
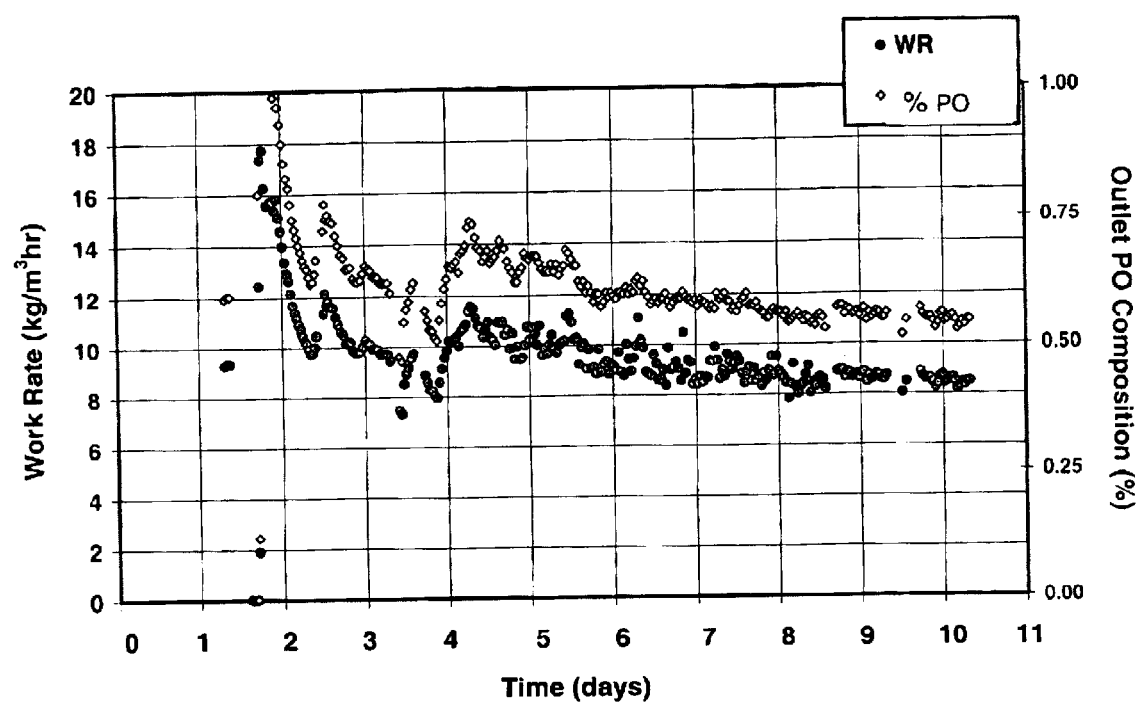
FIG. 3 shows catalyst activity, expressed as work rate (WR), and outlet propylene oxide composition (PO) in the production of propylene oxide using supports with the silver bonding additive.
Figure 4:
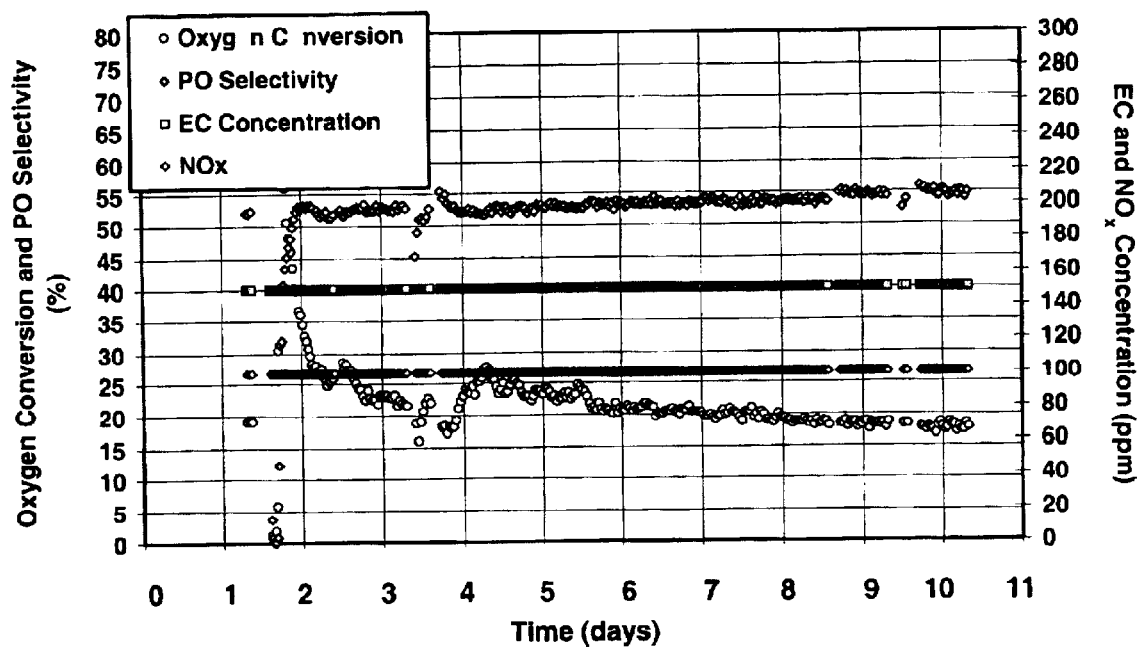
FIG. 4 shows the oxygen conversion, propylene oxide (PO) selectivity, ethylchloride (EC) concentration and $NO_x$ concentration, whereas $NO_x$ is a mixture of nitric oxide, nitrogen dioxide, and dinitrogen tetroxide, using supports with the silver bonding additive.

This Example demonstrates that the catalyst prepared on calcium carbonate/silver support exhibited superior performance in both activity, selectivity, and stability compared to the catalyst prepared on a pure calcium carbonate support. Catalyst AA (test number I) was prepared on the calcium carbonate support of Example 2 (comparative). In the course of catalyst preparation, the support was double impregnated with silver solution, and bonding additives were introduced in the third impregnation. The catalyst contained 15.5 wt % silver, 500 mmol/g potassium (introduced as potassium nitrate), 200 mmol/g sodium (introduced as sodium nitrate), and 50 mmol/g lithium (introduced as lithium hydroxide). Performance of this catalyst in the standard microreactor test (15 g catalyst in the tube, feed composed of 8% propylene, 12% oxygen, 150 ppm ethylenechloride, 100 ppm $NO_x$, balance $N_2$, GHSV 600 Nl/1·h, T=250° C.) is shown in FIGS. 1 and 2. (test number I). Catalyst BB was prepared on the calcium carbonate/silver support of Example 6 (of the invention) and tested similarly, except that the amount of silver introduced in the course of the double impregnation (in addition to silver already in the support) was 21 wt. % and that bonding additives were introduced simultaneously with silver during the second impregnation. Performance of the resulting catalyst is shown in FIGS. 3 and 4 (test number II). As can be seen, a PO selectivity of 55% is achieved with the catalyst as prepared according to the invention.

The supports of the present invention are useful in a variety of catalytic applications in which a reactant stream (gaseous or liquid) is contacted with a catalyst supported on a support at elevated temperatures. There are many such processes in the chemical industry but the present support has proved itself particularly suitable in the catalytic formation of alkylene oxide from a gas stream comprising ethylene and oxygen. The utility of the present invention is however not so limited.

We claim:

1. A process for preparing a catalyst which comprises:
   (a) preparing a paste comprising a uniform mixture of
      (i) at least one alkaline earth metal carbonate;
      (ii) a liquid medium;
      (iii) a silver bonding additive; and,
      (iv) at least one extrusion aid;
   (b) forming one or more shaped particles from said paste;
   (c) drying and calcining said particles; and,
   (d) impregnating the dried and calcined particles with a solution comprising a silver compound.

2. The process of claim 1, wherein the liquid medium is aqueous; and the silver bonding additive is a silver oxalate ethylenediamine complex.

3. The process of claim 1, wherein step (d) comprises a process comprising:
   (i) impregnating the particles obtained in step (c); and,
   (ii) drying the impregnated particles at a temperature in the range of from 100° C. to 1000° C.

4. The process of claim 2 wherein the paste has a weight ratio of silver calculated as metal to alkaline earth metal carbonate of 1:5 to 1:100; the silver solution has a concentration of silver of from 27% to 33% by weight, and the temperatures for drying and calcining are in the range of from 200° C. to 950° C.

5. The process of claim 2 wherein the alkaline earth metal carbonate comprises calcium carbonate; and, the paste comprises a mixture of between 0.90 to 99 parts by weight of calcium carbonate and between 35 to 45 parts by weight aqueous silver oxalate-ethylenediamine solution having a concentration of from 27% to 33% by weight of the silver complex.

6. The process of claim 2 wherein the silver oxalate ethylenediamine complex comprises an aqueous solution, wherein said solution further comprises cesium hydroxide.

7. The process of claim 1 wherein the alkaline earth metal carbonate comprises calcium carbonate.

8. The process of claim 7 wherein the silver bonding additive comprises an aqueous solution of a silver oxalate ethylenediamine complex; the weight ratio of silver to calcium carbonate in the catalyst is 1:9; and, the shaped particles are formed via extrusion.

9. A process for preparing an olefin oxide comprising reacting a gas composition comprising an olefin and oxygen in the presence of the catalyst composition obtained by the process comprising:
   (a) preparing a paste comprising a uniform mixture of
      (i) at least one alkaline earth metal carbonate;
      (ii) a liquid medium;
      (iii) a silver bonding additive; and,
      (iv) at least one extrusion aid;
      (v) forming one or more shaped particles from said paste;
      (vi) drying and calcining said particles; and,
      (vii) impregnating the dried and calcined particles with a solution comprising a silver compound.

10. The process of claim 9 wherein the olefin is propylene or ethylene.

11. The process of claim 9 wherein the gas composition further comprises ethylchloride and/or $NO_x$.

12. The process of claim 9 wherein the olefin has a concentration of at least 0.5% v, the concentration of oxygen is at least 2%, and the ethylchloride concentration is at least 0.1 ppm by volume.

13. The process of claim 9 wherein the process is operated at a temperature in the range of from 150° C. to 320° C., a pressure in the range of from 0.5 barg to 100 barg, and a Gas Hourly Space Velocity in the range of from 100 Nl/1·h to 30,000 Nl/1·h.

14. The process of claim 12 wherein the olefin is propylene or ethylene.

15. The process of claim 13 wherein the gas composition further comprises ethylchloride and/or $NO_x$.

16. The process claim 13 wherein the olefin has a concentration of at least 0.5% v, the concentration of oxygen is at least 2%, and the ethylchloride concentration is at least 0.1 ppm by volume.

* * * * *